(12) United States Patent
Yamamoto et al.

(10) Patent No.: US 8,173,425 B2
(45) Date of Patent: May 8, 2012

(54) FUSION PARTNER CELLS

(75) Inventors: Naomasa Yamamoto, Saitama (JP); Mizuho Kaneda, Kita-ku (JP)

(73) Assignees: Naomasa Yamamoto, Saitama (JP); Medical & Biological Laboratories Co., Ltd., Aichi (JP)

( * ) Notice: Subject to any disclaimer, the term of this patent is extended or adjusted under 35 U.S.C. 154(b) by 0 days.

(21) Appl. No.: 12/296,899

(22) PCT Filed: Apr. 13, 2007

(86) PCT No.: PCT/JP2007/058129
§ 371 (c)(1),
(2), (4) Date: Jan. 16, 2009

(87) PCT Pub. No.: WO2007/119808
PCT Pub. Date: Oct. 25, 2007

(65) Prior Publication Data
US 2010/0028946 A1 Feb. 4, 2010

(30) Foreign Application Priority Data
Apr. 13, 2006 (JP) .................. 2006-110889

(51) Int. Cl.
*C12N 5/00* (2006.01)
(52) U.S. Cl. ........................................ 435/346
(58) Field of Classification Search ................. None
See application file for complete search history.

(56) References Cited

U.S. PATENT DOCUMENTS

| | | | |
|---|---|---|---|
| 4,574,116 A | 3/1986 | Kaplan et al. | |
| 4,634,664 A | 1/1987 | Oestberg | |
| 4,977,081 A | 12/1990 | Raybould et al. | |
| 6,007,814 A * | 12/1999 | Scheinberg | 424/130.1 |
| 6,479,247 B1 * | 11/2002 | Hart | 435/7.21 |
| 6,759,045 B2 * | 7/2004 | Goldenberg et al. | 424/153.1 |
| 7,531,643 B2 * | 5/2009 | Fukushima et al. | 530/388.8 |

FOREIGN PATENT DOCUMENTS

| | | |
|---|---|---|
| EP | 1064551 | 1/2001 |
| JP | 61-124380 | 6/1986 |
| WO | 99/47929 | 9/1999 |

OTHER PUBLICATIONS

Carroll et al., "Mouse × human heterohybridomas as fusion partners with human B cell tumors" J Immunol Methods, (May 1, 1986) 89(1):61-72.
Flynn et al., "Generation of a sheep × mouse heterohybridoma cell li1989ne (1C6.3a6T.1D7) and evaluation of its use in the production of ovine monoclonal antibodies" J Immunol Methods, (Jul. 26, 1989) 121(2):237-47.
Jox et al., "Stable Nontumorigenic Phenotype of Somatic Cell Hybrids between Malignant Burkitt's Lymphoma Cells and Autologous EBV-immortalized B cells Despite Induction of Chromosomal Breakage and Loss" Cancer Res., (Nov. 1, 1998) 58(21):4930-9.
Kennedy et al., "Production and Characterization of Bovine Monoclonal Antibodies to Respiratory Syncytial Virus" J Gen Virol., (Dec. 1988) 69 (Pt 12):3023-32.
Raybould et al., "Production of Stable Rabbit-Mouse Hybridomas That Secrete Rabbit mAb of Defined Specificity" Science, (Jun. 24, 1988) 240(4860):1788-90.
Teng et al., "Construction and testing of mouse-human heteromyelomas for human monoclonal antibody production" Proc Natl Acad Sci USA, (Dec. 1983) 80(23):7308-12.
Thompson et al., "The efficient production of stable, human monoclonal antibody-secreting hybridomas from EBV-transformed lymphocytes using the mouse myeloma X63-Ag8.653 as a fusion partner" J Immunol Methods, (Nov. 20, 1986) 94(1-2):7-12.
Waldmann, "Monoclonal Antibodies in Diagnosis and Therapy" Science, (Jun. 21, 1991) 252(5013):1657-62.
Zanella et al., "New Heteromyeloma cell lines for the production of human monoclonal antibodies" J Immunol Methods (Dec. 8, 1992) 156(2):205-15.
Booman et al., "Construction of a Bovine-Murine Heteromyeloma Cell Line; Production of Bovine Monoclonal Antibodies against Rotavirus and Pregnant Mare Serum Gonadotrophin" Vet Immunol Immunopathol. Mar. 1990: 24(3):211-26.
Delvig et al., "Comparison of three human-murine heteromyeloma cell lines for formation of human hybridomas after electrofusion with human peripheral blood lymphocytes from meningococcal cases and carriers" Hum Antibodies Hybridomas. 1995: 6(2):42-6.
Faller et al., "HAB-1, a new heteromyeloma for continuous production of human monoclonal antibodies" Br J Cancer, Oct. 1990: 62(4):595-8.
Foung et al., "Rescue of Human Monoclonal Antibody Production from an EBV-Transformed B Cell Line by Fusion to a Human-Mouse Hybridoma" J Immunol Methods. May 11, 1984: 70(1):83-90.
Gorny et al., "Human Monoclonal Antibodies Specific for Conformation-Sensitive Epitopes of V3 Neutralize Human Immunodeficiency Virus Type 1 Primary Isolates from Various Clades" J Virol. Sep. 2002: 76(18):9035-45.
Grunow et al. "The high efficiency, human B cell immortalizing heteromyeloma CB-F7" J Immunol Methods. Feb. 10, 1998: 106(2):257-65.
Gustafsson et al., "SPAM-8, a mouse-human heteromyeloma fusion partner in the production of human monoclonal antibodies. Establishment of a human monoclonal antibody against cytomegalovirus" Hum Antibodies Hybridomas. Jan. 1991: 2(1):26-32.
Kudo et al., "Highly Efficient Procedure for Production of Human Monoclonal Antibodies: Establishment of Hybrids between Epstein-Barr Virus—Transformed B Lymphocytes and Heteromyeloma Cells by Use of GIT Culture Medium" Tohoku J Exp Med. Apr. 1988: 154(4):345-55.
Ostberg et al., "Human × (Mouse × Human) Hybridomas" Methods Enzymol. 1986:121:228-34.
Posner et al., "The Construction and Use of a Human-Mouse Myeloma Analogue Suitable for the Routine Production of Hybridomas Secreting Human Monoclonal Antibodies" Hybridoma. Dec. 1997: 6(6):611-25.

* cited by examiner

*Primary Examiner* — Michail Belyavskyi
(74) *Attorney, Agent, or Firm* — Karl Bozicevic; Bozicevic, Field & Francis LLP

(57) ABSTRACT

Fusion partner cells that enable production of heterohybridomas even from cells of species other than mouse were produced by fusing myeloma cells derived from a first animal species with leukemia cells derived from a second animal species, which have an extra S phase in the cell cycle and have the property of diploidizing. Stable production of substances can be achieved by producing heterohybridomas through cell fusion between the fusion partner cells and substance-producing cells of an animal other than mouse.

2 Claims, 10 Drawing Sheets

SPYMEG                    Karpas

ADHESION: WEAK ADHESIVE        ADHESION: ADHESIVE
PROLIFERATION: ++              PROLIFERATION: +

FUSION PARTNER CELLS

TECHNICAL FIELD

The present invention relates to fusion partner cells and hybridomas.

BACKGROUND ART

Hybridomas (fused cells) are used in producing substances using culture cells. There are many animal cells that produce commercially or academically useful substances. However, it is in general difficult to culture animal cells, and there is no technique for stably culturing animal cells for a long period while maintaining their ability to produce substances. Under such circumstances, a technique was proposed to create cells comprising both characteristics of the ability to grow in culture and the ability to produce substances. With this technique, hybridomas are made by fusing cells producing a biologically active substance and, as fusion partner cells, myeloma cells that can be passaged indefinitely and stably in vitro.

When monoclonal antibodies are produced by the cell fusion method, hybridomas are tested for their characteristics such as antibody productivity and binding activity and the selected cells are cloned to homogeneity. Then, the cells are grown to homogeneous cell populations to produce monoclonal antibodies. Such hybridomas are grown by in vitro or in vivo (in ascites) cultures and expanded to produce antibodies on a large scale. The method for developing monoclonal antibodies using the cell fusion method is already known (see Non-Patent Document 1). Monoclonal antibodies are believed to be more superior in specificity as compared to polyclonal antibodies purified from antisera. Thus, monoclonal antibodies are used as a powerful tool in various immunological assay methods.

When cells from the same species are fused, the fused cells are simply called "hybridomas". In general, mouse monoclonal antibodies and the like are produced by this method. On the other hand, antibody-producing cells obtained by fusing cells isolated from a particular species with immortalized cells derived from a different species are called "heterohybridomas". The term "heterohybrid" is synonymous with heterologous fusion, and the produced cells are called "heterohybridomas". Furthermore, antibody-producing cells produced by fusing cells derived from three animal species are called "triomas". Monoclonal antibodies produced by this method are rat and hamster antibodies. Heterohybridomas between mouse and rat or between mouse and hamster are produced by fusing mouse myeloma cells with lymphocytes derived from rats or hamsters to which an antigen of interest has been administered. Heterohybridomas thus obtained are cloned and provide monoclonal antibodies which are derived from each immunized animal.

To date, reports have been published on heterohybridomas producing human, rabbit, bovine, and sheep monoclonal antibodies (see Non-Patent Documents 2 to 5 and Patent Documents 1 and 2).

However, monoclonal antibody production by heterohybridomas is considered to be more difficult as the phylogenetic distance between the species of cells to be fused increases. For example, it is extremely difficult to produce antibodies using hybridomas between mouse and rabbit, or mouse and human. Since hybridomas have an aberrant number of chromosomes, segregation does not always distribute the same chromosome pairs to the daughter cells and some chromosomes may be lost.

Non-Patent Document 1: Waldman, T., Science 252:1657-1662 1991
Non-Patent Document 2: Proc. Natl. Acad. Sci. USA 80:7308-7312, 1983
Non-Patent Document 3: Raybould et al., Science 240:1788-1790, 1988
Non-Patent Document 4: Kennedy et al., J. Gen. Virol. 69:3023-3032, 1988
Non-Patent Document 5: Flynn et al., J. Immunol. Methods 121:237-246, 1989
Patent Document 1: U.S. Pat. No. 4,634,664 specification
Patent Document 2: U.S. Pat. No. 4,977,081 specification

DISCLOSURE OF THE INVENTION

Problems to be Solved by the Invention

An objective of the present invention is to provide techniques that enable stable and simple production of substances using hybridomas in a wide range of animal species. Specifically, the objective of the present invention is to provide novel fusion partners that are useful in producing hybridomas and methods for producing the fusion partners. Another objective of the present invention is to provide hybridomas obtained by fusing substance-producing cells and the fusion partners obtained according to the present invention, methods for producing the hybridomas, and methods for producing substances using the hybridomas.

Means for Solving the Problems

There have been various problems in producing substances using cell fusion techniques, except for some limited animals such as mice. For example, there is no useful cell which can be used as fusion partners in cell fusion, and this is an essential problem that has to be overcome in cell fusion techniques for other animals. The present inventors discovered that cells useful as fusion partners could be obtained by fusing particular types of cells. Stable hybridomas are provided by fusing non-murine cells with fusion partner cells established by the present inventors. The present inventors demonstrated that hybridomas thus obtained stably retained the phenotypes throughout the cloning process and were also useful as substance-producing cells. The present inventors thus completed the present invention. Furthermore, the present inventors demonstrated that antibodies that specifically recognized antigens could be produced by using the hybridomas of the present invention.

Specifically, the present invention relates to the fusion partner cells described below, and hybridomas between the fusion partner cells and substance-producing cells. The present invention also relates to methods for producing these cells and methods for producing substances using the hybridomas.

[1] a fusion partner cell that can be obtained by fusing:
 (a) a myeloma cell derived from a first animal species, and
 (b) a leukemia cell derived from a second animal species, whose cell cycle has an extra S phase;

[2] the fusion partner cell of [1], wherein the first animal species is mouse and the myeloma cell is selected from the group consisting of the mouse myeloma cell lines MOPC21, P3X63AG8, SP2/0, NS-1, P3.X63AG8.653, F0, S194/5.XXO.BU-1, FOX-NY, and SP2/0-Ag14, and cell lines derived from these cell lines;

[3] the fusion partner cell of [1], wherein the second animal species is human and the leukemia cell is selected from the group consisting of the leukemia cell lines MEG-01, HEL, UT-7, M07e, MEG-A2, and DAMI, and cell lines derived from these cell lines;

[4] the fusion partner cell of [1], wherein the myeloma cell derived from the first animal species is SP2/0-Ag14 and the leukemia cell derived from the second animal species is MEG-01;

[5] the fusion partner cell SPYMEG deposited under the accession number FERM BP-10761;

[6] a hybridoma that can be obtained by fusing:
(1) a fusion partner cell that can be obtained by fusing:
(a) a myeloma cell derived from a first animal species; and
(b) a leukemia cell derived from a second animal species, whose cell cycle has the an extra S phase; and
(2) a third cell;

[7] the hybridoma of [6], wherein the first animal species is mouse and the myeloma cell is selected from the group consisting of the mouse myeloma cell lines MOPC21, P3X63AG8, SP2/0, NS-1, P3.X63AG8.653, F0, S194/5.XXO.BU-1, FOX-NY, and SP2/0-Ag14, and cell lines derived from these cell lines;

[8] the hybridoma of [6], wherein the second animal species is human and the leukemia cell is selected from the group consisting of the leukemia cell lines MEG-01, HEL, UT-7, M07e, MEG-A2, and DAMI, and cell lines derived from these cell lines;

[9] the hybridoma of [6], wherein the myeloma cell derived from the first animal species is SP2/0-Ag14 and the leukemia cell derived from the second animal species is MEG-01;

[10] the hybridoma of [6], wherein the fusion partner cell is SPYMEG deposited under the accession number FERM BP-10761;

[11] the hybridoma of [6], wherein the third cell is a cell derived from the same animal species as that from which the leukemia cell derives;

[12] the hybridoma of [11], wherein the third cell is an antibody-producing cell;

[13] a method for producing a fusion partner cell, which comprises the steps of:
(1) fusing:
(a) a myeloma cell derived from a first animal species; and
(b) a leukemia cell derived from a second animal species, whose cell cycle has an extra S phase; and
(2) culturing the cell fused in step (1) and collecting the fusion partner cell from the culture;

[14] a method for producing a hybridoma, which comprises the steps of:
(1) fusing an antibody-producing cell with the fusion partner cell obtained by the method of [13]; and
(2) culturing the cell fused in step (1) and collecting hybridoma from the culture;

[15] a method for producing an antibody-producing cell, which comprises the steps of:
(1) obtaining a hybridoma by fusing an antibody-producing cell with the fusion partner cell obtained by the method of [13]; and
(2) collecting the hybridoma obtained in step (1) as an antibody-producing cell;

[16] the method of [15], which additionally comprises the step of cloning the hybridoma obtained in step (1);

[17] a method for producing an antibody, which comprises the steps of:
(1) obtaining a hybridoma by fusing an antibody-producing cell with the fusion partner cell obtained by the method of [13]; and
(2) culturing the hybridoma obtained in step (1) and collecting the antibody from the culture;

[18] the method of [17], which additionally comprises the step of cloning the hybridoma obtained in step (1);

[19] a method for producing an antibody against an infectious disease, which comprises the steps of:
(1) obtaining a hybridoma by fusing the fusion partner cell obtained by the method of [13] with an antibody-producing cell derived from a subject that has been exposed to a pathogenic antigen of an infectious disease; and
(2) culturing the hybridoma obtained in step (1) and collecting an antibody against the infectious disease from the culture; and

[20] the method of [19], wherein the infectious disease is influenza, AIDS, or viral hepatitis.

Alternatively, the present invention relates to the use of fused cells as fusion partner cells, which can be obtained by fusing the cells of (a) and (b) described below. Specifically, the present invention includes the use of the fused cells as fusion partner cells to be fused with antibody-producing cells.
(a) Myeloma cells derived from a first animal species; and
(b) leukemia cells derived from a second animal species, whose cell cycle has an extra S phase.

Effects of the Invention

The present invention provides fusion partner cells that enable production of stable hybridomas when fused with heterologous cells. Hybridomas obtained by cell fusion with the fusion partner cells of the present invention stably produce substances. In particular, cell fusion between antibody-producing cells and the fusion partner cells of the present invention yields hybridomas that produce antibodies that are derived from the antibody-producing cells. In a preferred embodiment, cell fusion between the fusion partner cells of the present invention and human or mouse antibody-producing cells yields hybridomas that produce human or mouse antibodies, respectively. Maintaining human antibody-producing cells was previously thought to be difficult. Thus, the present invention has the significant effect of providing cells that stably produce human antibodies.

The stable maintenance of phenotypes in hybridomas is an important feature not only in producing substances but also in cloning cells. For example, as antibody-producing cells, hybridomas are cloned to obtain monoclonal antibodies. Cell cloning means that a cell population is obtained from a single cell. Hence, it is very difficult to clone cells of interest if cell phenotypes are instable in the division cycles of single cells. Since the hybridomas provided by the present invention stably maintain their cell phenotypes, they can be readily cloned.

BEST MODE FOR CARRYING OUT THE INVENTION

Figure 1:
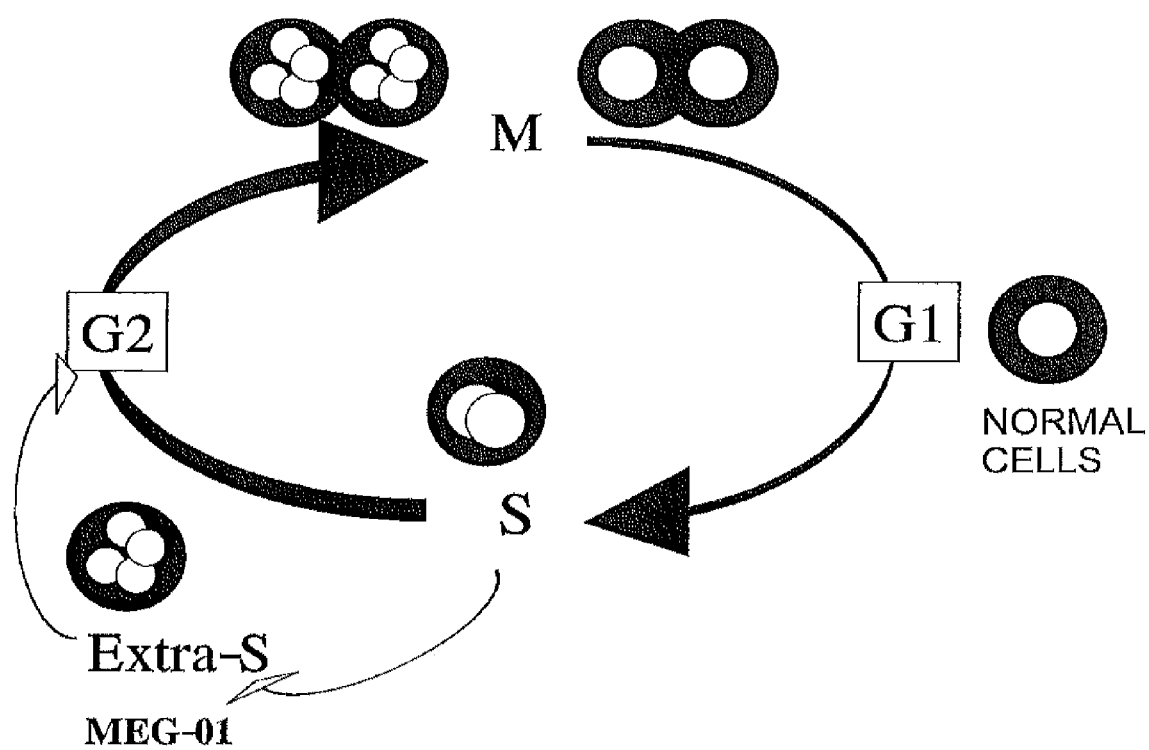
FIG. 1 is a diagram showing the cell cycle of MEG-01.

Herein, "hybridoma" refers to a cell obtained by cell fusion. In general, hybridomas are produced by fusing heterologous cells, or cells that are homologous but derived from different animals or tissues. Hybridomas also include cells resulting from fusion of homologous cells of an identical cell type. Furthermore, the hybridomas of the present invention also include fused cells obtained by fusing two or more cells. Specifically, the hybridomas of the present invention also include fused cell β obtained by fusing cell C with hybridoma α resulting from cell fusion between cell A and cell B.

(cell $A$)×(cell $B$)=[hybridoma α]

[hybridoma α]×(cell $C$)=[hybridoma β]

where the three types of cells, namely cell A, cell B, and cell C, which are fused to yield hybridoma β, may be derived from any animal species. Accordingly, in the present invention, the species from which the cells are derived may be identical or may be different. In particular, hybridomas obtained by fusing three types of cells are occasionally referred to as "triomas".

In a preferred embodiment of the present invention, the species of cell A (the first cell) and cell B (the second cell) are different from each other, while the species of cell B and cell C (the third cell) are the same. The hybridomas of the present invention also include fused cells obtained when the species of cell A and cell C are the same or the species of cell A, cell B, and cell C are different from one another.

In general, cells that are obtained by cell fusion and can be readily passaged in vitro for a long period are particularly called "hybridomas". Accordingly, preferred hybridomas of the present invention are cells that can be readily passaged in vitro for a long period after cell fusion. Alternatively, the preferred hybridomas of the present invention are cells that continue to grow after limiting dilution. In other words, cells that continue to grow after limiting dilution are included in the cells that can be readily passaged in vitro for a long period after cell fusion.

Furthermore, the preferred hybridomas of the present invention are cells that maintain the phenotype of the cells used in cell fusion. In the present invention, cell phenotypes that are to be maintained in hybridomas include the ability of cells to produce substances. For example, when the cells used in cell fusion produce an antibody or cytokine, preferred hybridomas of the present invention maintain the ability to produce these substances.

However, the hybridomas of the present invention do not necessarily maintain all phenotypes of the cells used in cell fusion. Thus, when maintenance of other phenotypes, for example, production of cell surface antigens, or enzymes and transcription factors that are accumulated in cells are desired, in addition to the production of the above-described antibodies, these phenotypes are also included in the phenotypes to be maintained by the hybridomas. However, when production of such substances is not necessary, hybridomas lacking the ability to produce the substances are also included in the hybridomas of the present invention as long as they continue to produce necessary substances.

Herein, "fusion partner cells" refer to cells that enable production of hybridomas when fused with other cells. Preferred fusion partner cells of the present invention enable cells to survive in vitro for a long period after cell fusion.

Furthermore, fusion partner cells preferably have appropriate selection markers for screening. A selection marker refers to a phenotype that allows (or does not allow) survival under particular culture conditions.

Known animal cell selection markers include hypoxanthine-aminopterin-thymidine sensitivity (hereinafter abbreviated as "HAT sensitivity"), resulting from hypoxanthine-guanine phosphoribosyltransferase deficiency (hereinafter abbreviated as "HGPRT deficiency") or thymidine kinase deficiency (hereinafter abbreviated as "TK deficiency"). In HAT selection medium, HAT-sensitive cells cannot synthesize DNA and thus will die. However, when fused with normal cells, the resulting cells can continue to synthesize DNA via the salvage pathway originating from the normal cells and thus can grow even in HAT selection medium.

HGPRT- or TK-deficient cells can be selected using medium containing 6-thioguanine, 8-azaguanine (hereinafter abbreviated as "8AG"), or 5'-bromodeoxyuridine. Normal cells are killed due to incorporation of these pyrimidine analogs into DNA. In contrast, cells lacking these enzymes can survive in the selection medium because they do not allow incorporation of these pyrimidine analogs. Another selection marker called G418 resistance confers resistance to 2-deoxystreptamine antibiotics (gentamicin analogs) due to the neomycin resistance gene.

The present invention provides fusion partner cells that can be obtained by fusing:
  (a) myeloma cells derived from a first animal species; and
  (b) leukemia cells derived from a second animal species, whose cell cycle has an extra S phase.

The present invention also provides methods for producing fusion partner cells, which comprise the steps of:
  (1) fusing:
    (a) myeloma cells derived from a first animal species; and
    (b) leukemia cells derived from a second animal species, whose cell cycle has an extra S phase; and
  (2) culturing the cells fused in step (1) and collecting the fusion partner cells from the culture.

Herein, myeloma cells derived from a first animal species means cells deriving from myelomas, which can be cloned independently. The phrase "can be cloned independently" means that growth can be commenced even from a single cell and passaging can be continuously done under artificial culture conditions.

In the present invention, the myeloma cells derived from the first animal species may be any cells, as long as they provide fusion partners when fused with leukemia cells.

Known cells that can be used as the myeloma cells of the present invention include, for example, those described below. In the cell line listing below, "ATCC" represents an accession number in American Tissue and Culture Collection, while "JCRB" represents an accession number in JCRB cell bank (Japanese Collection of Research Bioresources). Accordingly, all of the cell lines are available from the cell banks. The cell lines in JCRB cell bank are distributed via Health Science Research Resources Bank (HSRRB).

MOPC21 (ATCC number: HB-8411)
P3X63AG8 (ATCC number: T1B9)
SP2/0 (ATCC number: CRL 1581)
NS-1 (ATCC number: TIB18)
P3.X63AG8.653 (ATCC number: CRL 1580)
F0 (ATCC number: CRL 1646)
S194/5.XXO.BU-1 (ATCC number: CRL 1580)
FOX-NY (ATCC number: CRL 1732)
SP2/0-Ag14 (JCRB number: 0029)

Of these cell lines, those having the preferred characteristics described above are the group of mouse myeloma cell lines and cell lines derived from these mouse myeloma cell lines. The derived cell lines mean cell lines that are recloned after introducing additional phenotypes such as drug resistance.

In the present invention, the leukemia cells derived from the second animal species are leukemia cells whose cell cycle has an extra S phase. The general cell cycle of eukaryotic cells is shown below. Growing cells continue to divide while repeating the cycle from the G1 phase to the M phase. The cell growth is stopped when cell cycle reaches a stable state called the G0 phase after the M phase.

-[G1 Phase]-[S Phase]-[G2 Phase]-[M Phase]-

In each cell cycle, the S phase is a period of nucleic acid synthesis. In this period, it is thought that the genomic DNA constituting the chromosome is replicated and the cell is prepared for cell division. The genomic DNA doubled in the M phase is segregated into two cells by mitosis. However, a phenomenon was observed in particular cells, where the cell cycle did not proceed to the stage of cell division after replication of genomic DNA. The post-DNA synthesis period where the cell cycle does not proceed to cell division in the M phase was named the "extra S phase". The undivided cells were found to accumulate synthesized genomic DNA and thus contain an increased amount of DNA. For example, the average number of chromosomes in MEG-01, which is a leukemia cell line preferred in the present invention, is 2 n=104. This is much larger than the chromosome number of normal cells (2 n=46). The reason is that MEG-01 has an extra S phase in its cell cycle that increases genomic DNA and thus has the property of diploidizing (Oncogene 13:695-703, 1996) (FIG. 1).

Thus, the present invention is expected to have the effect of preventing the loss of chromosomes derived from the antibody-producing cells in heterohybridomas by using leukemia cells that have an extra S phase in their cell cycle and the property of diploidizing.

In the present invention, the leukemia cells whose cell cycle has an extra S phase are derived from a species which is different from that from which the above-described myeloma derives, and preferably the same as that from which the third cell described below derives. Such leukemia cells can be obtained from hematopoietic tissues or peripheral blood of animals with leukemia. The hematopoietic tissues include bone marrow, spleen, lymph nodes, and the like. Leukemia includes, for example, megakaryocytic leukemia. Leukocytes, mononuclear cells, or such can be separated, for example, by centrifuging peripheral blood and collecting cell fractions with a particular specific gravity by the Ficoll method.

Furthermore, whether the separated leukemia cells have an extra S phase in their cell cycle can be assessed by using as an indicator the increase of chromosomes in the cells. The increase of chromosomes can be confirmed, for example, based on the increase in the ploidy (the total number of chromosomes) of cells treated with 12-O-tetradecanoyl-phorbol-13-acetate (TPA). Such increases in the ploidy can be detected with a flow cytometer or ploidy analyzer.

Alternatively, known leukemia cells may also be used in the present invention. Known cells that can be used as the leukemia cells derived from the second animal species in the present invention include, for example, the cell lines indicated below. MEG-01 and HEL are human megakaryocytic leukemia cell lines (Blood 66:1384-1392, 1985; J. Clin. Invest. 85:1072-1084).

MEG-01 (ATCC No. CRL-2021)
HEL (JCRB No. 0062)
UT-7 (N. Komatsu et al., Cancer Res. 51: 341-348, 1991)
M07e (Avanzi G C et al., J. Cell Physiol. December 1990; 145(3):458-64)
MEG-A2 (JCRB No. IFO50478)
DAMI (Blood 89:4238, 1997)

In particular, MEG-01 shows 8AG resistance, which is useful as a selection marker. Furthermore, since MEG-01 produces no immunoglobulin, it is preferred as a partner in fusion with antibody-producing cells to prepare hybridomas.

The fusion partner cells of the present invention can be obtained by cell fusion between myeloma cells derived from a first animal species and leukemia cells derived from a second animal species, whose cell cycle has an extra S phase. Known cell fusion techniques such as the polyethylene glycol (PEG) method and electrofusion can be used to achieve cell fusion.

The polyethylene glycol method is conducted according to the following procedure. First, the ratio between myeloma and leukemia cells is optimized depending on each particular fusion condition. Those skilled in the art can select the optimal concentration of polyethylene glycol (PEG) based on the molecular weight of PEG or such. For example, 35% PEG1500 (Aldrich, Milwaukee, Wis.) is one of requirements for general cell fusion. 1 ml of 35% PEG1500 is slowly added to cell pellet/cell mixture over a period of 1.5 minutes. Then, the cell suspension is gradually diluted with serum-free medium and then serum-containing medium to achieve cell fusion.

Other convenient methods that can also be used to achieve cell fusion include electrofusion. In this method, cells are placed in a special buffer and then aligned by applying voltage. The aligned cells can be efficiently fused together due to an increased chance of contact with each other.

The fusion mixture is suspended, for example, at a cell density of $8 \times 10^5$ cells/ml in 150 ml of HB-GRO medium (Irvine Scientific, Santa Ana, Calif.) containing 15% fetal calf serum. The cells are then aliquoted at $2.0 \times 10^5$ cells/well into 96-well plates. The cells can be incubated under an atmosphere of 5% to 10% $CO_2$ at 37° C. to obtain 8AG-resistant fusion partner cells. The resulting fusion partner cells can be cloned, if required. The cloned fusion partner cells contribute to the maintenance of reproducibility in producing hybridomas.

For example, SP2/0-Ag14 can be used as the myeloma cell derived from the first animal species, while MEG-01 can be used as the leukemia cell derived from the second animal species, whose cell cycle has an extra S phase.

The fusion partner cells provided as described above, can themselves be passaged for a long period, and thus can be used as general fusion partner cells to obtain monoclonal antibodies from antibody-producing cells. Specifically, like mouse myeloma lines established to produce mouse homo-hybridomas, the cells can be used as fusion partners that enable stable provision of hybridomas using antibody-producing cells derived from species other than mouse. Among fusion partner cells obtained according to the present invention, the fusion partner cell SPYMEG yielded by fusing the mouse myeloma cell line SP2/0-Ag14 with the human leukemia cell line MEG-01 was deposited under the accession number FERM BP-10761 in the International Patent Organism Depositary.

(a) Name and address of depositary institution

Name: National Institute of Advanced Industrial Science and Technology, International Patent Organism Depositary Address: (Postal code: 305-8566) Central 6, 1-1-1 Higashi, Tsukuba-shi, Ibaraki-ken, Japan (b) Date of deposit: Feb. 24, 2006

(c) Acceptance Number: FERM BP-10761

(transferred from FERM P-20816 deposited on Feb. 24, 2006)

The present invention relates to hybridomas that can be obtained using the fusion partner cells described above. Specifically, the present invention provides hybridomas that can be obtained by fusing:

(1) fusion partner cells that can be obtained by fusing:
(a) myeloma cells derived from a first animal species; and
(b) leukemia cells derived from a second animal species, whose cell cycle has an extra S phase; and
(2) a third cell.

The present invention also provides methods for producing hybridomas, which comprise the steps of:

(1) fusing:
(a) myeloma cells derived from a first animal species; and
(b) leukemia cells derived from a second animal species, whose cell cycle has an extra S phase;
(2) culturing the cells fused in step (1) and collecting the fusion partner cells from the culture;
(3) fusing a third cell with the fusion partner cells collected in step (2); and
(4) culturing the cells fused in step (3) and collecting hybridomas from the culture.

The species of the third cell of the present invention is same or different from the species of the first cell or the second cell. Specifically, it is possible to use cells from humans, rabbits, mice, rats, bovines, goats, sheep, or such. More specifically, when fusion partners obtained from mouse myeloma (the first cell) and human leukemia cells (the second cell) are used, the third cell is preferably derived from human or mouse. In particular, the fact that human cells can be used as the third cell is a major advantage of the fusion partner cells of the present invention.

The third cell of the present invention is a cell that is expected to ultimately enable long-term culture. More specifically, for example, cells having the ability to produce substances of interest can be used as the third cell. Hybridomas that enable long-term maintenance of cells having a phenotype of interest can be obtained through cell fusion between the above-described cells and the fusion partner of the present invention. The formation of hybridomas that enable long-term maintenance of cells is generally called "immortalization".

In the present invention, any cell producing a biologically active substance of interest may be used as the third cell. Preferred biologically active substances of the present invention include antibodies. In other words, antibody-producing cells are preferred as the third cell of the present invention. Antibody-producing cells include, for example, leukocytes (peripheral lymphocytes) and spleen cells. Methods for collecting such cells from a living body are known. More specific examples of the third cell include antibody-producing cells derived from animals having a history of exposure to a pathogenic antigen of an infectious disease. Animals having a history of exposure to a pathogenic antigen of an infectious disease include animals vaccinated with a pathogenic antigen (vaccine) of an infectious disease and animals that have experienced an infection. Herein, the infectious disease is not particularly limited; however, preferred examples include influenza, AIDS, and viral hepatitis such as HCV and HBV.

In particular, peripheral blood lymphocytes are preferred as the antibody-producing cells of the present invention. Peripheral blood lymphocytes can be readily obtained by collecting blood. Hybridomas producing mouse antibodies can be readily obtained by preparing hybridomas from mouse peripheral blood lymphocytes according to the present invention. Alternatively, hybridomas producing human antibodies can be readily obtained by preparing hybridomas from human peripheral blood lymphocytes according to the present invention.

In the present invention, the fusion partner can be fused with the third cell by the same method as that used in cell fusion between the first and second cells described above. Cell fusion can be achieved by using the PEG method or electrofusion. For example, when human peripheral blood lymphocytes are fused with SPYMEG as the fusion partner of the present invention, the preferred conditions include the following conditions.

First, the number of peripheral blood leukocytes (PBLs) to be fused is preferably adjusted to $1\times10^7$ to $10^8$ cells. SPYMEG and PBL are combined together at a ratio of 2:1 to 10:1. The cells are precipitated by centrifugation, and the resulting supernatant is removed. Polyethylene glycol (PEG) is added to the collected cell fraction to fuse the cells. The concentration of PEG used in cell fusion is 30% to 70%, preferably 40% to 60%, and more preferably 50%. Depending on the number of cells, 0.1 to 2.0 ml, preferably 0.6 to 1.0 ml of a PEG solution is added to the cells over a period of 60 to 90 seconds while mixing using a pipette. After the PEG solution is added, the cell suspension is continuously mixed with the pipette for further two to three minutes. Then, 10 to 14 ml of serum-free medium is added little by little while mixing over a period of 30 to 60 seconds. A serum-free medium is then added, and the mixture is centrifuged. After centrifugation, the supernatant is removed and the cells are washed once with serum-free medium. The washed cells are suspended in HAT medium (RPMI containing 15% FBS and HAT (×50)) and plated into 96-well plates.

Serum-free media and PEG that are generally used in cell fusion by those skilled in the art can be suitably employed. For example, the media and PEG listed below can be used in cell fusion of the present invention.

PEG: PEG1500 (Aldrich, Milwaukee, Wis.)

HAT: HAT supplement (50×) (GIBCO; Cat. No. 21060-017)

Serum-free medium: RPMI1640 (SIGMA; Cat. No. R8758)

Alternatively, antibody-producing cells may also be obtained from immunized animals. Animals are immunized in advance with an arbitrary antigen along with an appropriate adjuvant. The antigen may be conjugated with a carrier protein, and then used as an immunogen. Such carrier proteins for preparing the immunogen include keyhole limpet hemocyanin (KLH) and bovine serum albumin (BSA). In general, animals to be immunized include rabbits, mice, rats, goats, and sheep. Conventional adjuvants include Freund's complete adjuvant (FCA) (Adv. Tubercl. Res. 1:130-148, 1956). The antibody titer is monitored by ELISA or Ouchterlony method. After the titer is confirmed to be elevated to a satisfactory level, the antibody-producing cells are collected. The antibody-producing cells suspended are used in cell fusion. Antibody-producing cells can be obtained by collecting spleen cells or peripheral blood lymphocytes by the same procedure as that used for human cells. Antibody-producing cells thus obtained can be fused with fusion partners of the present invention to prepare hybridomas of the present invention.

As described above, antibodies can be produced by using antibody-producing cells as the third cell in the methods of the present invention for producing hybridomas. Specifically, the present invention provides methods for producing antibodies, which comprise the steps of:
(1) obtaining fusion partner cells via the steps of:
(A) fusing:
(a) myeloma cells derived from a first animal species; and
(b) leukemia cells derived from a second animal species, whose cell cycle has an extra S phase: and
(B) culturing the cells fused in step (A) and collecting the fusion partner cells from the culture;
(2) obtaining hybridomas by fusing antibody-producing cells with the fusion partner cells obtained in step (1); and
(3) culturing the hybridomas obtained in step (2) and collecting the antibodies from the culture.

Alternatively, the present invention relates to methods for preparing the above-described antibody-producing cells which are useful in producing antibodies. Specifically, the present invention provides methods for preparing antibody-producing cells, which comprise the steps of:
(1) preparing fusion partner cells via the steps of:
(A) fusing:
(a) myeloma cells derived from a first animal species; and
(b) leukemia cells derived from a second animal species, whose cell cycle has an extra S phase; and
(B) culturing the cells fused in step (A) and collecting the fusion partner cells from the culture;
(2) preparing hybridomas by re-fusing antibody-producing cells with the fusion partner cells prepared in step (1); and
(3) collecting the hybridomas prepared in step (2) as antibody-producing cells.

Hybridomas that stably produce antibodies can be obtained by using the fusion partner cells of the present invention. Successfully fused cells can be preferentially proliferated by culturing the hybridomas in an appropriate selection medium. For example, HAT-containing selection media can be used when SPYMEG of the present invention is used as fusion partner cells.

The methods of the present invention for producing antibodies or antibody-producing cells may comprise cloning hybridomas. Methods for cloning hybridomas are known. Specifically, hybridomas can be cloned by the limiting dilution method. Theoretically, hybridomas diluted by limiting dilution form cell populations each of which is grown from a single cell. Such a cell population has homogeneous genetic characteristics, and thus is a clone. Antibody obtained from a cloned hybridoma is called monoclonal antibody. Monoclonal antibodies have highly uniform antigen binding properties.

Specifically, the present invention provides methods for producing monoclonal antibodies, which comprise the steps of:
(1) preparing fusion partner cells via the steps of:
(A) fusing:
(a) myeloma cells derived from a first animal species; and
(b) leukemia cells derived from a second animal species, whose cell cycle has an extra S phase; and
(B) culturing the cells fused in step (A) and collecting the fusion partner cells from the culture;
(2) preparing hybridomas by fusing antibody-producing cells with the fusion partner cells prepared in step (1) and cloning hybridomas producing antibodies of interest; and
(3) culturing hybridomas cloned in step (2) and collecting monoclonal antibodies from the culture.

The present invention also relates to methods for producing antibody-producing cells that are useful in producing the antibodies described above. Specifically, the present invention provides methods for producing antibody-producing cells, which comprise the steps of:
(1) preparing fusion partner cells via the steps of:
(A) fusing:
(a) myeloma cells derived from a first animal species; and
(b) leukemia cells derived from a second animal species, whose cell cycle has the extra S phase; and
(B) culturing the cells fused in step (A) and collecting the fusion partner cells from the culture;
(2) preparing hybridomas by re-fusing antibody-producing cells with the fusion partner cells prepared in step (1); and
(3) obtaining antibody-producing cells from the hybridomas prepared in step (2).

Antibody-producing cells can be cloned in the present invention. Monoclonal antibody-producing cells can be obtained by cloning antibody-producing cells that produce antibodies of interest. Specifically, the present invention provides methods for producing hybridomas that produce monoclonal antibodies, which comprise the steps of:
(1) preparing fusion partner cells via the steps of:
(A) fusing:
(a) myeloma cells derived from a first animal species; and
(b) leukemia cells derived from a second animal species, whose cell cycle has an extra S phase; and
(B) culturing the cells fused in step (A) and collecting the fusion partner cells from the culture;
(2) preparing hybridomas by re-fusing antibody-producing cells with the fusion partner cells prepared in step (1) and cloning hybridomas producing antibodies of interest; and
(3) collecting as antibody-producing cells the hybridomas cloned in step (2).

The hybridomas of the present invention are antibody-producing cells having a stable ability to produce antibodies in vitro. Thus, the cells can be grown in an appropriate medium while retaining the ability to produce antibodies, although they are heterohybridomas. Therefore loss of vital clones during the cloning process is less likely. In addition, established hybridoma clones can be maintained stably.

Antibodies or monoclonal antibodies can be produced by culturing hybridomas or their clones obtained according to the present invention. Serum-free media or media containing a low concentration of serum are preferably used because of the convenience of antibody purification. Basal media for animal cell culture include DMEM, RPMI1640, and ASF 103. Alternatively, hybridomas or their clones may be inoculated into the peritoneal cavity of nude mice or SCID mice to collect monoclonal antibodies as ascites.

Culture media may be supplemented with 5% to 10% v/v fetal bovine serum (hereinafter abbreviated as "FCS"). When hybridomas of the present invention are cultured in such culture media, known factors that enhance antibody production are advantageously added to the media. Agents that enhance antibody production in vitro include, for example, D-penicillamine, acetoacetic acid, biguanide agents, vitamin K5, N-acetylglutamic acid (Japanese Patent Application Kokai Publication No. (JP-A) H8-70858 (unexamined, published Japanese patent application), interleukin 6 (Nature 324 (6092):73-6, 1986), sugar alcohols (JP-A (Kokai) H2-200177), lipopolysaccharides (JP-A (Kokai) H4-20294), phorbol ester (JP-A (Kokai) H1-171494), and butyric acid (hybridoma 4(1):63, 1985). Monoclonal antibodies thus obtained can be purified by salting out such as using ammonium sulfate or sodium sulfate, ion exchange chromatography, gel filtration, affinity chromatography, and such.

The present invention is specifically illustrated below with reference to Examples, but it is not to be construed as being limited thereto.

All prior art documents cited herein are incorporated herein by reference.

EXAMPLES

Example 1

Preparation of Fusion Partner Cells

Cells of SP2/0-Ag-14 ($3 \times 10^7$ cells) and MEG-01 (3 to $6 \times 10^7$ cells) were cultured in RPMI supplemented with 5% FCS (standard medium), and then fused together according to the conventional method using PEG. The fused cells were cultured in the standard medium (RPMI supplemented with 5% FCS) for three days. The medium was changed with FCS-free RPMI on day 3, and then the cells were cultured for 19 days. The cells were diluted with the standard medium containing 8AG by limiting dilution on day 19, and then cultured for five days. The proliferated fused cells were collected and named "fusion partner cell SPYMEG". SPYMEG was deposited under the accession number FERM BP-10761 (transferred from FERM P-20816) on Feb. 24, 2006 in the National Institute of Advanced Industrial Science and Technology, International Patent Organism Depositary. SPYMEG was resistant to 8AG, and was killed when cultured in the HAT medium.

Example 2

Preparation of Heterohybridomas by the PEG Method (a) Collection of Human Peripheral Blood Leukocytes (Density Centrifugation)

Human peripheral blood (40 ml) was collected using heparin and aliquoted (10 ml) into 50 ml tubes. 25 ml of sterile PBC was added to each tube. After mixing, the blood was overlaid onto a 15-ml aliquot of HISTOPAQUE (SIGMA H8889) in 50 ml tubes. The tubes were centrifuged at 800 rpm and room temperature for 30 minutes. After centrifugation, the leukocyte layers were collected.

(b) Collection of Fusion Partner Cells (SPYMEG)

SPYMEG cells were grown in 75-cm² culture flasks (medium: RPMI containing 10% FBS) and collected.

(c) Cell Fusion

The collected human peripheral blood leukocytes and SPYMEG cells were combined at a ratio of 2:1 to 10:1 and then centrifuged. 4 to $8 \times 10^7$ cells were obtained from 40 ml of peripheral blood. SPYMEG was cultured using four 75-cm² flasks. 0.6 to 1.0 ml of 50% PEG (PEG4000; MERCK, Cat. No. 1097270100 was diluted with an equal volume of RPMI (RPMI1640; SIGMA, Cat. No. R8758)) was added to the pellet to perform cell fusion. After washing with serum-free RPMI, the cells were suspended in 160 ml of 1% BM containing 15% FBS (EQUITECH-BIO INC., Lot. SFB30-1548) and HAT (HAT supplement (BM-condimed; Roche, Cat. No. 663573) (50×), GIBCO Cat. No. 21060-017) and plated into eight 96-well plates. The medium was changed three days after plating. When hybridoma colonies were confirmed to be formed (after two to three weeks), the culture supernatants were sampled from the 96-well plates for the first screening.

Example 3

IgG Purification Protocol

The samples (culture supernatants) were eluted at a flow rate of 1 drop/second. The flow-through fractions were collected. The columns were washed with PBS containing 0.1% $NaN_3$ at the maximal flow rate (washed until absorbance at 280 became 0.05 or lower while monitoring with a spectrophotometer). The columns were eluted with two to five column bed volumes of 0.17 M glycine-HCl buffer (pH 2.3) at the maximal flow rate. Using a fraction collector, the eluate was collected into test tubes containing 1 M Tris-HCl buffer (pH 8.0) of a volume of one fifth or larger than the elution fraction volume (ml). The eluted fractions were mixed with the neutralization Tris buffer (1 M Tris-HCl buffer (pH 8.0)) as soon as possible. After measurement of A280 of each fraction, the fractions were surveyed for proteins. Fractions with A280 of 0.1 or greater were pooled.

After pooling, the pH was confirmed to be 8.0 using a pH test strip. The purity of the pool was assessed by SDS-PAGE using 12.5% gel and sample buffer (2ME+). Each lane contained 5 µg of a sample. The same amount of a previous batch was also electrophoresed for comparison. The pooled solution was packed into a dialysis tube and dialyzed against PBS or PBS containing 0.1% $NaN_3$ with a volume 100 times or more of that of the pooled solution. The dialysis was repeated three times or more and each dialysis was carried out for six hours or more. After concentration, the dialysis tube was washed thoroughly with deionized water. After the dialysis tube was gently rubbed well to dissolve protein adhering to the tube wall, the concentrated solution was removed from the tube. Then, the concentration was measured.

Alternatively, without using a fraction collector, the eluted solution may be collected into a measuring cylinder, beaker, or the like, while stirring. Even in this case, the neutralization Tris buffer (1 M Tris-HCl buffer (pH 8.0)) is used with a volume of one fifth or more of the elution fraction volume (ml). After collection, the pH is confirmed to be 8.0 using a pH test strip. If the pH is lower than 8.0, it is adjusted to 8.0 immediately by adding the neutralization buffer.

Example 4

Measurement of Human IgG by ELISA (a) Preparation of Sensitized Plates

A rabbit anti-human IgG polyclonal antibody was diluted to 10 µg/ml with a sensitization buffer (PBS) and aliquoted (50 µl/well) into microplates (Nunc MaxiSorp). The plates were allowed to stand at 4° C. overnight. The sensitization buffer was removed and remaining liquid was removed by tapping the plates. A blocking buffer (PBS containing 1%

BSA and 0.1% NaN$_3$) was added (100 μl/well) and the plates were allowed to stand at 4° C. overnight.

(b) ELISA

Figure 2:
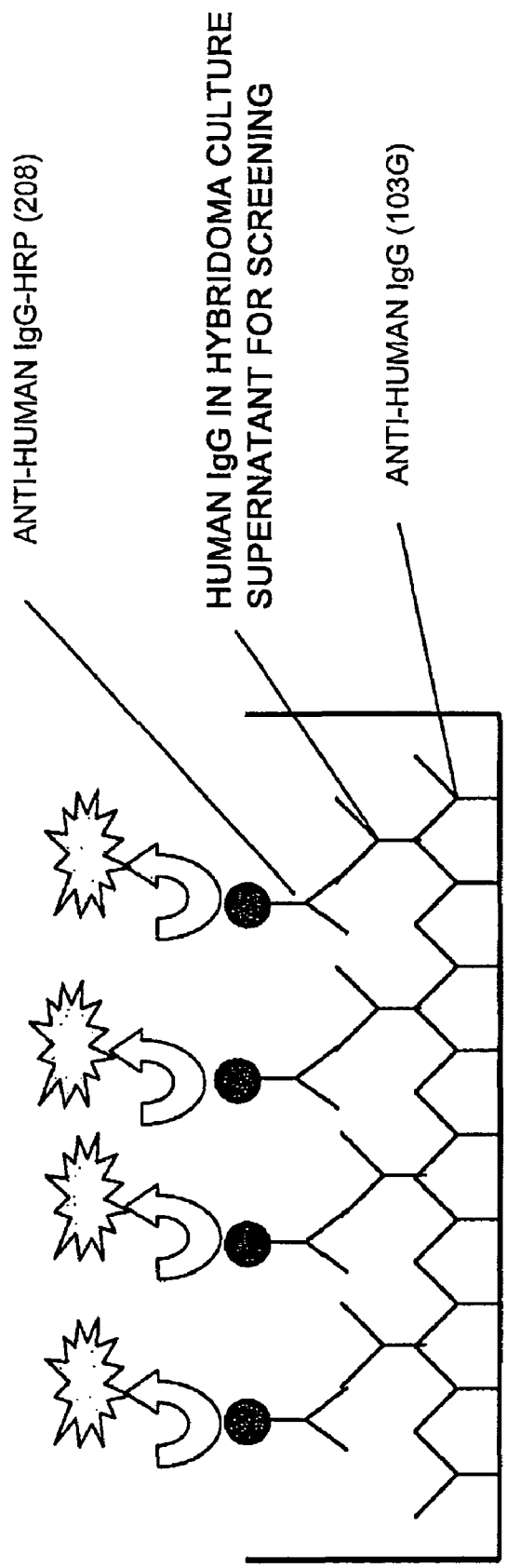
FIG. 2 is a diagram showing the scheme of ELISA screening for human IgG-producing hybridomas.

Hybridoma culture supernatants were aliquoted (50 μl/well) into sensitized microplates (prepared as described in (a)). The plates were incubated and allowed to stand at room temperature for one hour. The reaction solution was removed and the plates were washed three times with a washing buffer (PBS containing 0.05% Tween20). Remaining liquid was removed by tapping the plates. A labeled antibody was diluted (peroxidase-labeled; 5,000 times diluted and then used; POD-labeled anti-human IgG polyclonal antibody) and aliquoted (50 μl/well) into the plates. Then, the plates were allowed to stand at room temperature for one hour. A substrate (tetramethylbenzidine) solution was prepared. The labeled antibody solution was removed from the plates. After washing three times with washing buffer, remaining liquid was removed by tapping the plates. The substrate solution was aliquoted (50 μl/well). The plates were incubated at room temperature for about 15 minutes. A reaction termination solution (2N H$_2$SO$_4$) was aliquoted (50 μl/well) into the plates. Absorbance (main wavelength, 450 nm; sub wavelength, 620 nm) was measured with a plate reader. The schematic diagram of ELISA used in this experiment is shown in FIG. 2.

Example 5

Confirmation of Human IgG by Western Blotting

A solution of 1 mg/ml antibody was combined with an equal volume of sample buffer. The resulting mixture was boiled for five minutes. 10 μl of the mixture (5 μg of antibody) was loaded onto a 12.5% gel. SDS-PAGE was carried out and the sample was transferred onto a PVDF membrane (Immobilon-P Cat. No. IPVH00010). The membrane was blocked with PBS containing 2% skimmed milk at 4° C. overnight, and then treated with PBS containing 10% BlockAce and anti-rat IgG POD×2500 as a detection antibody at room temperature for one hour. The membrane was washed three times with a buffer (PBS containing 0.05% Tween20). The substrate used was PIERCE (super signal West Pico Chemiluminescent Substrate, code 34080). After a minute of exposure, the film (Hyperfilm ECL; Amersham Bioscience, Cat. No. RPN3103K) was developed using RENDOL (Fuji Film) as a developer. The stop solution and fixer used were 3% acetic acid and RENFIX (Fuji Film), respectively.

Example 6

Results (a) Preparation of Fusion Partner Cells

Figure 3:
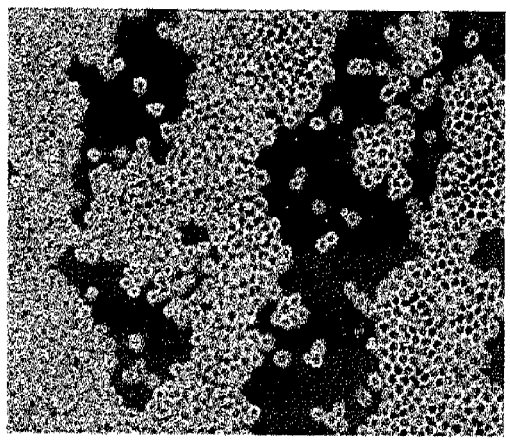
FIG. 3 shows photographs depicting a morphological comparison between the fusion partner cell of the present invention, SPYMEG and a known fusion partner cell, Karpas.
Figure 3:
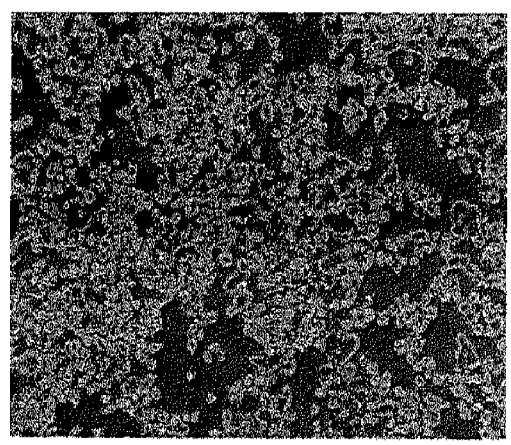

The prepared fusion partner cell line SPYMEG was evaluated (FIG. 3) by comparing it with a known human fusion partner cell line, Karpas (Abraham Karpas et al., Proc. Natl. Acad. Sci. USA Feb. 13, 2001; 98(4):1799-1804). Like other standard mouse myeloma cells, SPYMEG cells were spherical. The adhesion was weaker than that of Karpas. The growth activity was stronger (data not shown). These findings suggest that the performance of SPYMEG as a fusion partner cell is higher than that of Karpas. Furthermore, the established fusion partner cell line SPYMEG was viable even after freezing and stable without loss of the production ability even after a 100 ml scale culture for one month (data not shown).

(b) Preparation of Hybridomas (Antibody-Producing Cells) by Fusing SPYMEG Cells and Human Peripheral Blood Leukocytes Table 1 shows IgG production by hybridomas (antibody-producing cells) prepared by fusing SPYMEG cells and human peripheral blood leukocytes. The hybridomas were plated into eight 96-well microplates (768 wells). Table 1 shows the number of wells positive for colony formation, the number of wells positive for IgG production among them, and the number of wells positive for continuous IgG production over a period of three weeks or more among them. Screening was performed by ELISA.

This result demonstrates that IgG-producing hybridomas were prepared in this experiment. Furthermore, no IgG-producing clone could be obtained by using the known fusion partner cell line Karpas. This finding suggests that SPYMEG is a fusion partner cell line that enables more efficient production of hybridomas than Karpas.

TABLE 1

| | WELL POSITIVE FOR COLONY FORMATION | WELL POSITIVE FOR IgG PRODUCTION | NUMBER OF IgG-PRODUCING CLONES (BEFORE LD; CULTURED FOR THREE WEEKS OR MORE) |
|---|---|---|---|
| M. K 1 | 230/768 | 73/230 | 31/73 |
| K. 0 1 | 261/768 | 80/261 | 40/80 |
| M. K 2 | 205/768 | 47/205 | 26/47 |
| T. M 1 | 178/768 | 40/178 | NONE |
| karpas (T. M 1) | 10/768 | 2/10 | 0 |

Figure 4:
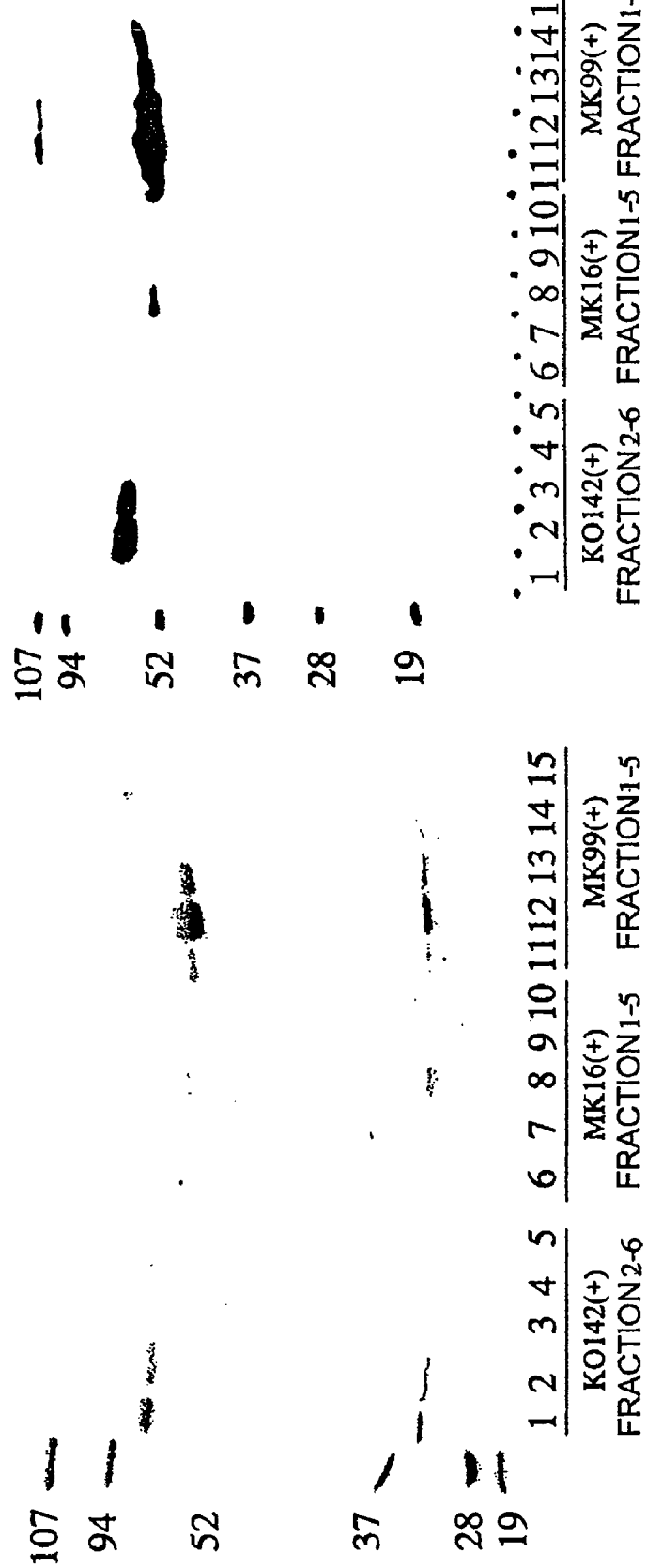
FIG. 4 shows photographs depicting the confirmation of IgG in each elution fraction of clones KO142(+), MK16(+), and MK99(+). In these photographs, (+) and (−) indicate ELISA-positive and -negative clones, respectively.

IgG-producing clones were loaded onto a protein G column. Fractions eluted from the column were assessed by SDS-PAGE and Western blotting (FIG. 4). In this figure, (+) and (−) indicate ELISA-positive and -negative clones, respectively. KO142 fraction 2 was positive in ELISA, and SDS-PAGE demonstrated the presence of human IgG in this fraction; however, the signal was undetectable by Western blotting. It was assumed that the detection failed for some reason.

Figure 5:
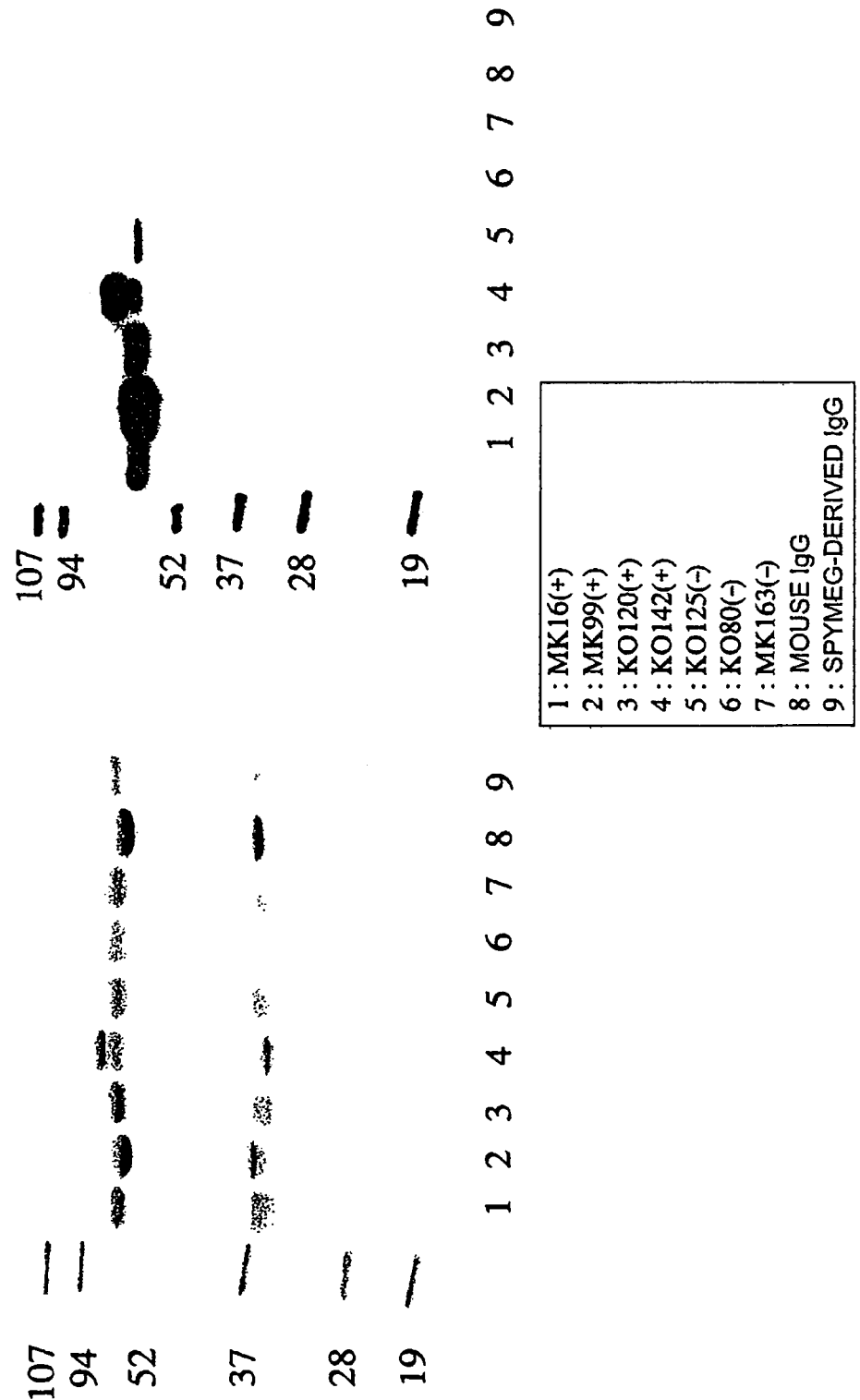
FIG. 5 shows photographs depicting the confirmation of IgG in the sample after dialysis and concentration of elution fraction of each clone.

Furthermore, eluted fractions of each clone were dialyzed and concentrated, and the resulting samples were tested (FIG. 5). In SDS-PAGE, bands suspected to correspond to IgG H and L chains were found even for ELISA-negative clones; however, the bands were not detectable by Western blotting using an anti-human IgG antibody, and were thus thought to correspond to IgG derived from FBS. A band was detected in lane 5 for an ELISA-negative clone. This clone was thought to produce IgG at a very low level, considering that it was judged to be negative based on the ELISA result for the culture supernatant. Furthermore, the result described above demonstrates that SPYMEG itself does not produce human IgG.

Table 2 shows the yield of IgG purified from the culture supernatant of each positive clone. When calculated based on the amount of IgG purified from 100 ml of culture supernatant, the concentration of human IgG in each culture supernatant was 2 to 11 μg/ml. Thus, the concentration was confirmed to be comparable to that for a standard mouse hybridoma.

TABLE 2

| | VOLUME OF CULTURE SUPERNATANT (ml) | CONCENTRATION (mg/ml) | LIQUID VOLUME (ml) | YIELD (mg) | CONCENTRATION OF IgG IN CULTURE SUPERNATANT (μg/ml) |
|---|---|---|---|---|---|
| MK16(+) | 100 | 0.329 | 0.6 | 0.1974 | 1.974 |
| MK99(+) | 100 | 0.572 | 2 | 1.144 | 11.44 |
| KO120(+) | 100 | 0.317 | 1 | 0.317 | 3.17 |
| KO142(+) | 100 | 0.616 | 0.6 | 0.3696 | 3.696 |

Example 7

Improvement of Method for Preparing Heterohybridomas

Figure 6:
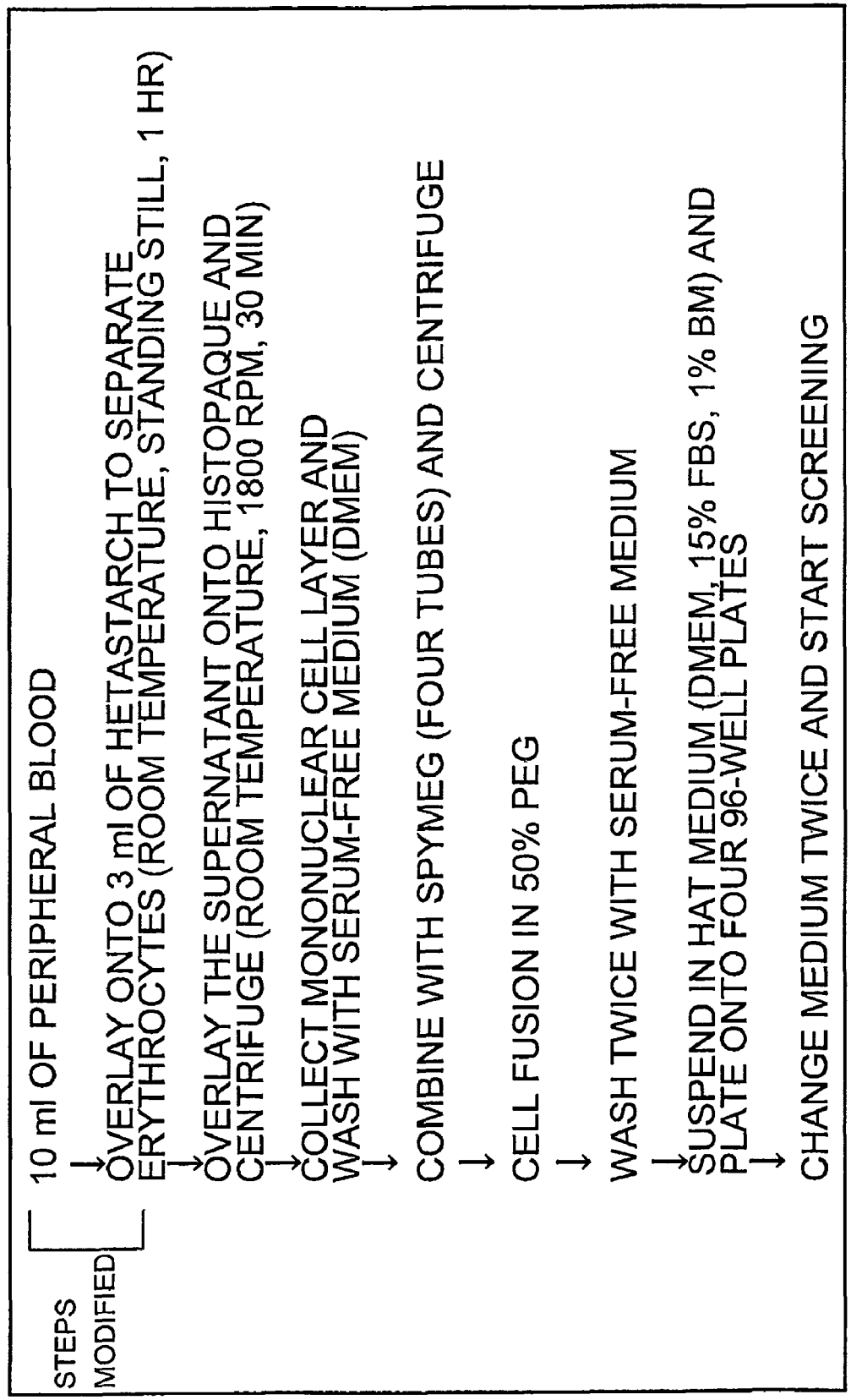
FIG. 6 is a diagram showing each step of the improved cell fusion method using SPYMEG.

In Example 2, peripheral blood diluted with PBS was overlaid onto HISTOPAQUE, followed by centrifugation. However, to obtain leukocytes (B cells) with higher purity, human peripheral blood leukocytes were collected by removing erythrocytes as a pretreatment by mixing peripheral blood with HetaSep (HETASTARCH), and then overlaying the blood onto HISTOPAQUE (FIG. 6).

Specifically, about 10 ml of peripheral blood derived from a patient inoculated with influenza HA vaccine was transferred into a 15-ml tube, and 2 to 3 ml of HetaSep (StemCell Technologies Inc., CAT #07906) was added thereto. The blood was mixed by inversion, and then allowed to stand at room temperature for one hour. The resulting supernatant (orange color) was collected, and HISTOPAQUE was overlaid onto it in a 15 ml tube slowly using a Pasteur pipette, taking care not to disturb the interface. The tube was centrifuged at 1,800 rpm and room temperature for 30 minutes. After centrifugation, the white band-like layer (leukocyte layer) formed in the middle of the solution was collected into a 50 ml tube with a Pasteur pipette. About 30 ml of serum-free DMEM was added, and the resulting mixture was centrifuged at 1,600 rpm for eight minutes to wash the cells.

As a fusion partner, SPYMEG cells were fused with human peripheral blood leukocytes collected by the method described in Example 2. Instead of RRMI, serum-free DMEM was used as a basal medium for the cell fusion.

Figure 7:
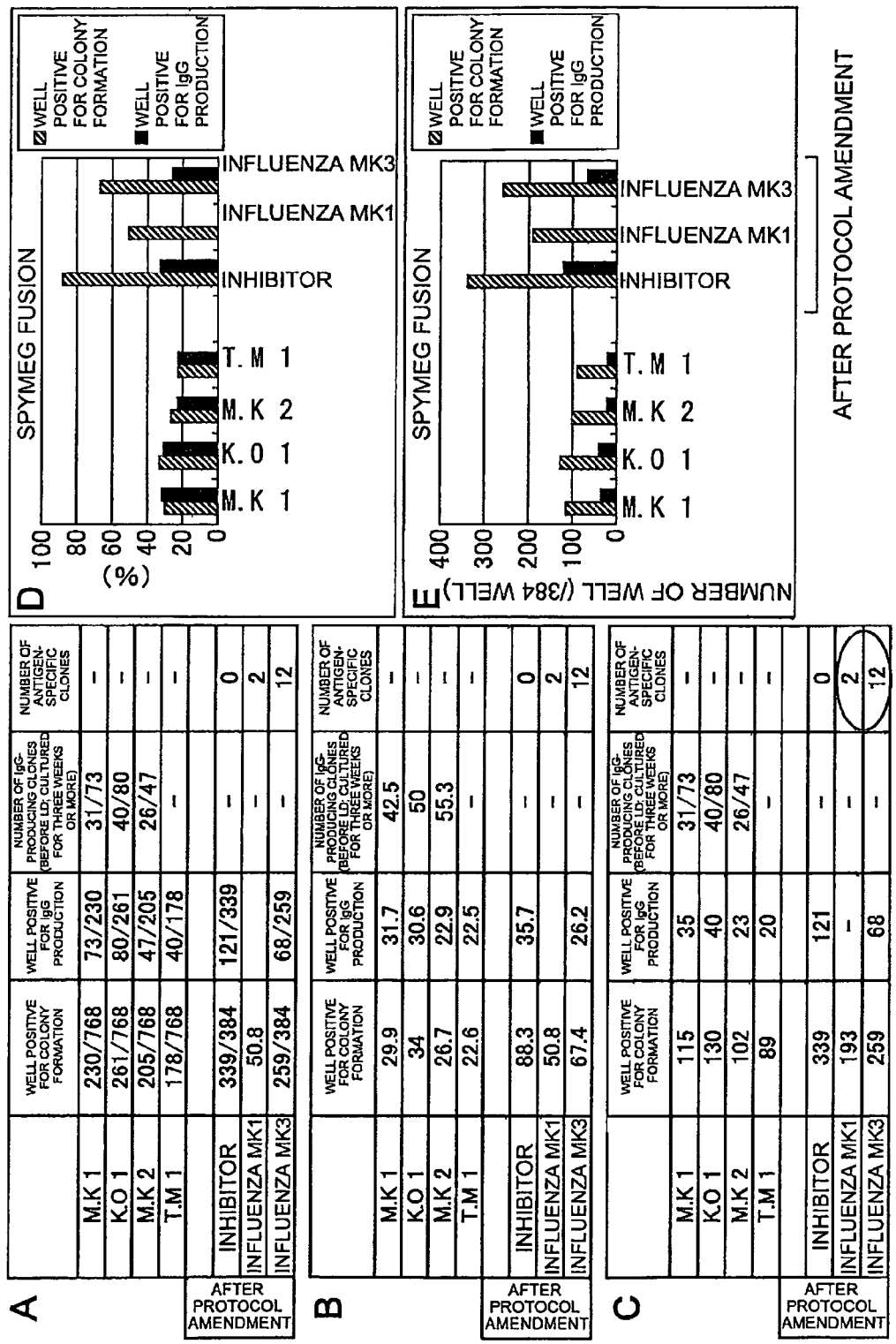
FIG. 7 is a diagram showing a comparison of the numbers of formed colonies and IgG-producing clones between before and after improving the cell fusion method. The number of wells positive for colony formation and the number of wells positive for IgG production in four 96-well plates are shown. Both of the numbers of wells positive for colony formation and for IgG production were significantly increased by improving the step of cell fusion. From the wells, multiple antibodies that specifically recognized influenza vaccine were obtained via influenza screening. Thus, antibodies that specifically recognized the antigen were successfully established for the first time.

IgGs were purified from the prepared heterohybridomas and the human IgGs were assessed by ELISA using the methods described in Examples 3 and 4. The result showed that both colonies formed after cell fusion and IgG-producing clones were increased as a result of improving the method for producing heterohybridomas (FIG. 7).

Example 8

Confirmation of Reactivity to Influenza Vaccine

IgG-producing clones prepared by the method described in Example 7 were confirmed to be reactive to influenza vaccine. Specifically, IgG production in each clone was assessed by sandwich ELISA as described below using plates sensitized with influenza vaccine and non-sensitized plates that were only blocked to remove clones exhibiting a nonspecific reaction.

Influenza vaccine was diluted 30 times with PBS and aliquoted (50 μl/well) into ELISA plates. The plates were allowed to stand overnight (sensitization). The influenza vaccine used was influenza HA vaccine (The Chemo-Sero-Therapeutic Research Institute, Japan). Influenza A and B virus strains were separately cultured in embryonated hen eggs. The allantoic fluid containing propagated virus was purified and concentrated by sucrose density gradient centrifugation or such. The viral particles were treated with ether or the like to prepare hemagglutinin (hereinafter abbreviated as "HA") suspension fractions. After inactivation with formalin, the preparation was diluted using phosphate-buffered sodium chloride solution so that it contained a pre-determined amount of HA of each viral strain.

After the solution was removed, 200 μl of the blocking buffer was added to each well. The plates were allowed to stand overnight (blocking). The blocking buffer was removed, and hybridoma culture supernatants were added (50 μl/well) to the plates. The plates were incubated at room temperature for one hour. The supernatants were removed and the wells were washed three times with PBS containing 0.05% Tween.

An HRP-labeled anti-human IgG antibody (MBL: 206) was diluted 5,000 times and added to the plates. The plates were incubated at room temperature for one hour. After washing three times, 50 μl of chromogenic substrate was added to each well. After 15 minutes of incubation for color development, a stop solution was added and the absorbance (OD450) was measured with a plate reader.

Figure 8:
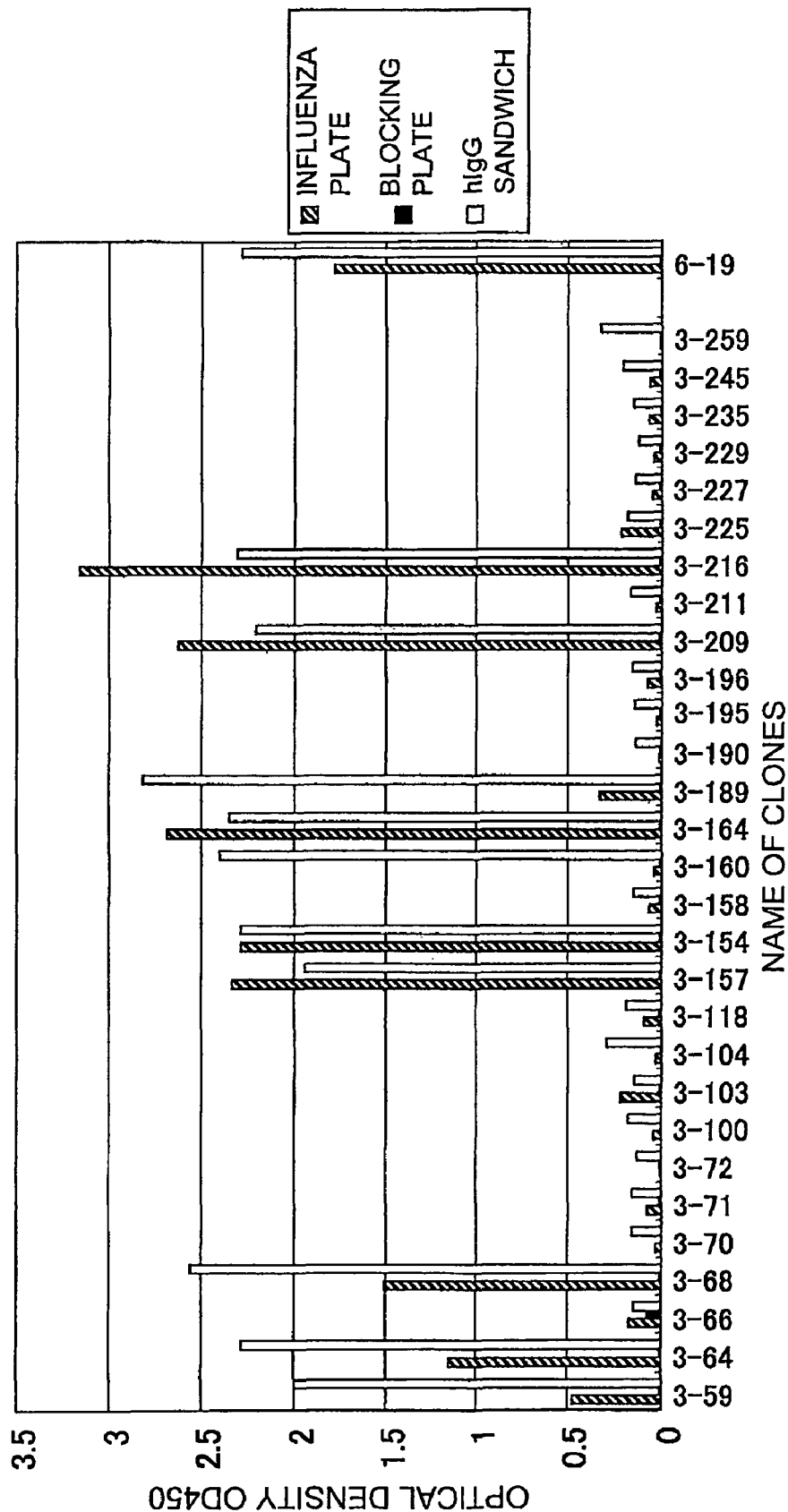
FIG. 8 is a diagram showing the reactivity of IgG-producing clones to influenza in ELISA.

As a result, about ten clones were found to be reactive to the influenza vaccine (FIG. 8). Antigen-specific human antibodies were successfully established by using the heterohybridomas of the present invention.

Example 9

Confirmation of Human IgG by Western Blotting

The reactivity of culture supernatants of human IgG-producing hybridomas was assessed by Western blotting using influenza HA vaccine as a sample.

Influenza HA vaccine was combined with an equal volume of sample buffer. The mixture was boiled for five minutes. 20 μl of the mixture (10 μl vaccine) was loaded onto 12.5% gel. SDS-PAGE was carried out and the sample was transferred onto a PVDF membrane (Immobilon-P Cat. No. IPVH00010). The membrane was blocked with PBS containing 2% skimmed milk at 4° C. overnight, and then treated with PBS containing 10% BlockAce and anti-human IgG-HRP (MBL code 206)×3000 as a detection antibody at room temperature for one hour. The membrane was washed three times with a buffer (PBS containing 0.05% Tween20). The substrate used was PIERCE (super signal West Pico Chemiluminescent Substrate, code 34080). After one minute of exposure, the film (Hyperfilm ECL; Amersham Bioscience, Cat. No. RPN3103K) was developed using RENDOL (Fuji Film) as a developer. The stop solution and fixer used were 3% acetic acid and RENFIX (Fuji Film), respectively.

Figure 9:
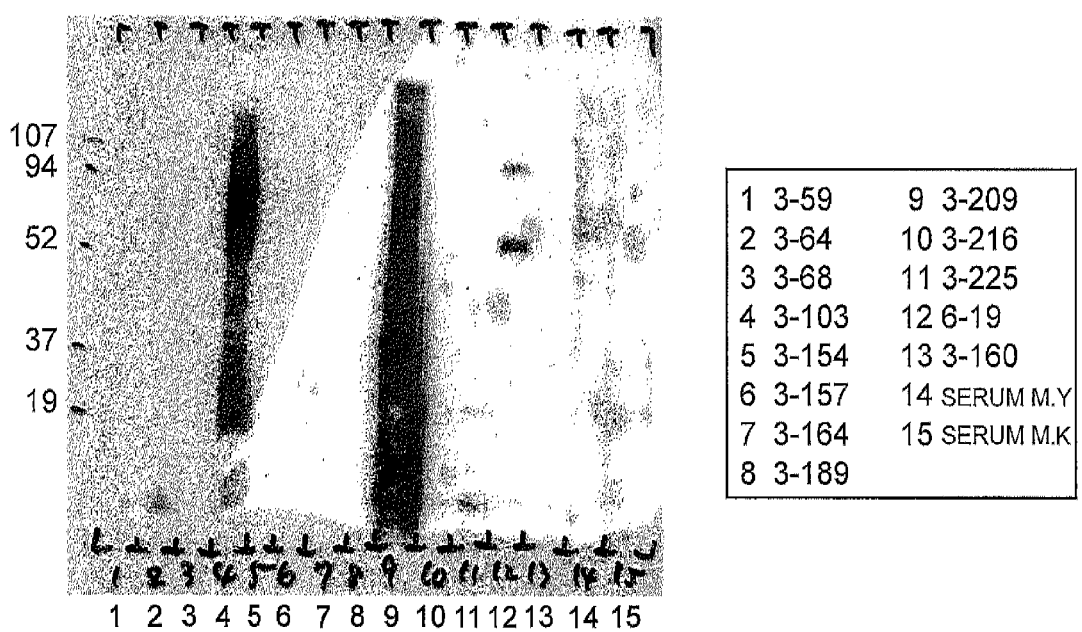
FIG. 9 is a photograph showing a Western blot to assess the reactivity to influenza vaccine.

As a result, a specific band was detected for clone (6-19) (FIG. 9).

Example 10

SDS-PAGE of Purified Human IgG (6-19) and Confirmation of its Reactivity

First, using the procedure described below, human IgGs reactive to influenza HA vaccine were purified from the culture supernatants of human IgG-producing hybridomas, which were demonstrated to be reactive by Western blotting as described in Example 9.

Figure 10:
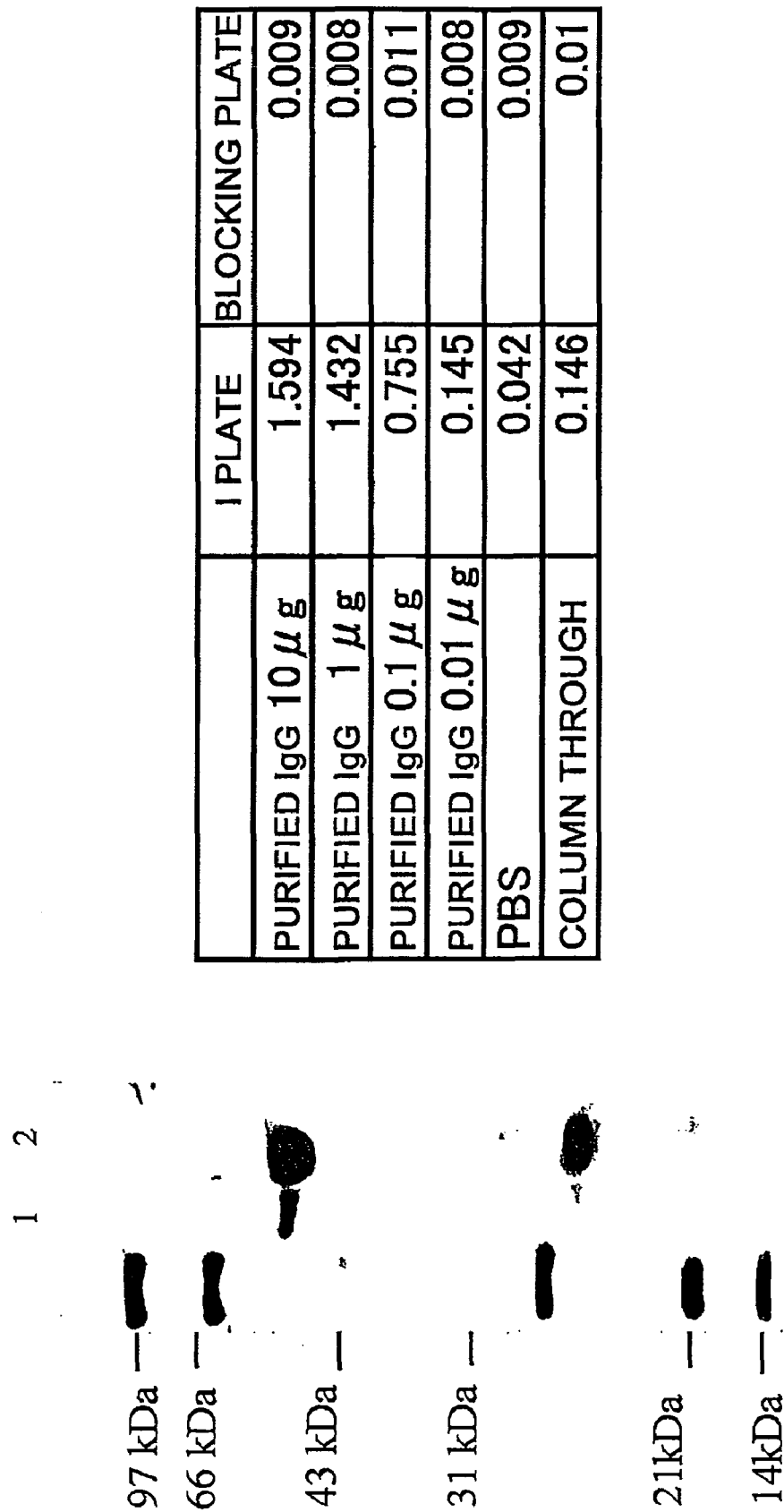
FIG. 10 is a photograph showing SDS-PAGE of purified human IgG (6-19) and confirmation of its reactivity. The values indicated in the Table are absorbance at the wavelength of 450 nm in ELISA using plates sensitized with influenza HA vaccine.

The culture supernatants were eluted at a flow rate of 1 drop/second. The flow-through fractions were collected. The column (Protein G Sepharose (Protein G Sepharose 4 Fast Flow, Cat. No. 17-0618-03)) was washed with PBS containing 0.1% $NaN_3$ at the maximal flow rate (washed until absorbance at 280 became 0.05 or lower while monitoring with a spectrophotometer). The column was eluted with two to five column bed volumes of 0.17 M glycine-HCl buffer (pH 2.3) at the maximal flow rate. Using a fraction collector, the eluate was collected into test tubes containing 1 M Tris-HCl buffer (pH 8.0) of a volume of one fifth or more than the elution fraction volume (ml). The eluted fractions were mixed with buffer as soon as possible. After measurement of A280 of each fraction, the fractions were surveyed for protein. Fractions with A280 of 0.1 or greater were pooled. After pooling, the pH was confirmed to be 8.0 using a pH test strip. The purity of the pool was assessed by SDS-PAGE using 12.5% gel and sample buffer (2ME+) (FIG. 10). The pool of fractions was packed into a dialysis tube and dialyzed against PBS or PBS containing 0.1% $NaN_3$ with a volume 100 times or more of that of the pooled solution. The dialysis was repeated three or more times, and each dialysis was carried out for six hours or more. After concentration, the dialysis tube was washed thoroughly with deionized water. After the dialysis tube was gently rubbed well to solubilize protein adhering to the tube wall, the concentrated solution was removed from the tube. Then, the concentration of the concentrated solution was measured.

The result showed that 2.5 mg of purified IgG was obtained from 200 ml of culture supernatant (FIG. 10) and the IgG retained the binding activity.

INDUSTRIAL APPLICABILITY

The present invention is useful in producing substances using animal cells. Specifically, hybridomas that can be readily cultured in vitro can be obtained by fusing the fusion partner of the present invention with cells producing useful substances. Such cells producing useful substances include antibody-producing cells.

Specifically, the present invention is useful as methods for producing antibodies. In particular, the present invention enables production of hybridomas using human antibody-producing cells as material. Hybridomas obtained according to the present invention stably produce human antibodies. For example, blood from patients who recovered from infectious diseases is very likely to contain cells producing antibodies that neutralize the pathogenic agents or toxins produced by the agents. Antibodies that are useful in treating infectious diseases can be produced by preparing hybridomas from antibody-producing cells of such patients according to the present invention.

Infectious diseases for which therapeutic antibodies can be obtained according to the present invention include, for example, influenza, AIDS, and viral hepatitis such as HCV and HBV.

Furthermore, antibody-producing cells of cancer patients are likely to include cells producing antibodies that have the activity of damaging cancer cells. Antibodies effective in treating cancer can be obtained by producing hybridomas from such antibody-producing cells according to the present invention.

Human antibodies can be obtained from human antibody-producing cells by using the antibody-producing methods of the present invention. Since human antibodies can be safely administered to humans, they are suitable as therapeutic antibodies. Modifications such as chimerization and humanization are required in treating humans with antibodies obtained from mice that are commonly used as a tool for producing monoclonal antibodies. When compared to such modifications, the antibody-producing methods of the present invention are obviously useful as methods for producing therapeutic antibodies.

The invention claimed is:

1. A fusion partner cell obtained by fusing:
    (a) a myeloma cell line SP2/O-Ag14, with
    (b) a leukemia cell MEG-01 to obtain a fusion partner cell line deposited under accession number FERM BP-10761 in the International Patent Organism Depository.

2. The fusion partner cell of claim 1, wherein the fusion partner cell is obtained by cultivating the fusion partner cell obtained in a cell culture and collecting the fusion partner cell from the culture.

* * * * *